United States Patent [19]

Fujita et al.

[11] Patent Number: 5,342,967
[45] Date of Patent: Aug. 30, 1994

[54] CRYSTAL MODIFICATIONS OF 2-M-TOLUIDINO-3-METHYL-6-DI-N-BUTYLAMINOFLUORAN, PROCESS FOR PREPARING THEREOF, AND RECORDING MATERIALS CONTAINING SAID CRYSTAL MODIFICATIONS

[75] Inventors: Shigeo Fujita, Osaka; Mansuke Matsumoto, Hyogo; Yojiro Kumagae, Osaka; Sayuri Wada, Osaka; Shuichi Hashimoto, Osaka, all of Japan

[73] Assignee: Yamamoto Chemicals, Inc., Osaka, Japan

[21] Appl. No.: 922,847

[22] Filed: Jul. 31, 1992

[30] Foreign Application Priority Data

Aug. 1, 1991 [JP] Japan ................... 3-193246

[51] Int. Cl.$^5$ .......................................... C07D 311/88
[52] U.S. Cl. .......................................................... 549/226
[58] Field of Search ............................................ 549/226

[56] References Cited

U.S. PATENT DOCUMENTS

| | | | |
|---|---|---|---|
| 4,330,473 | 5/1982 | Hatano et al. | 549/226 |
| 4,502,068 | 2/1985 | Taniguchi et al. | 503/216 |

FOREIGN PATENT DOCUMENTS

| | | |
|---|---|---|
| 410206 | 7/1990 | European Pat. Off. . |
| 435149 | 12/1990 | European Pat. Off. . |
| 462480 | 6/1991 | European Pat. Off. . |
| 466040 | 7/1991 | European Pat. Off. . |
| 477623 | 9/1991 | European Pat. Off. . |
| 49-17490 | 5/1974 | Japan . |
| 49-32767 | 9/1974 | Japan . |
| 178792 | 11/1982 | Japan . |
| 208092 | 12/1983 | Japan . |
| 59-68295 | 4/1984 | Japan . |
| 123556 | 7/1985 | Japan . |
| 116586 | 6/1986 | Japan . |
| 152486 | 7/1986 | Japan . |
| 1283183 | 11/1989 | Japan . |
| 1357244 | 6/1974 | United Kingdom . |

*Primary Examiner*—C. Warren Ivy
*Assistant Examiner*—A. A. Owens
*Attorney, Agent, or Firm*—Browdy and Neimark

[57] ABSTRACT

The improved two types of crystal modification of 2-n-toluidino-3-methyl-6-di-n-butylaminofluoran, as well as the crystalline toluene adduct thereof have high solubility in inner-phase solvent(s). Recording materials that use those compounds as electron donating color formers exhibit particularly good performance in various characteristics such as whiteness of the background, its storage stability, color rendition, sensitivity for color formation and image storage stability.

10 Claims, 6 Drawing Sheets

CRYSTAL MODIFICATIONS OF 2-M-TOLUIDINO-3-METHYL-6-DI-N-BUTYLAMINOFLUORAN, PROCESS FOR PREPARING THEREOF, AND RECORDING MATERIALS CONTAINING SAID CRYSTAL MODIFICATIONS

BACKGROUND OF THE INVENTION

This invention relates to crystal modifications or a crystalline toluene adduct (crystal having toluene of crystallization) of a fluoran compound that are useful as electron donating color formers in recording materials such as a pressure-sensitive recording material and a thermal recording material. The invention also relates to recording materials containing said crystal modifications and/or a crystalline toluene adduct, as well as a process for producing a specified crystal modification or a crystalline toluene adduct from said crystal modifications and/or crystalline toluene adduct.

Recording materials that make use of the color forming reaction between colorless or pale-colored electron donating color formers (hereunder referred to simply as "color formers") and organic or Inorganic electron accepting color developers (hereunder referred to simply as "color developers") are well known and classified as pressure-sensitive recording materials, thermal recording materials, electrothermal recording materials, etc. Pressure-sensitive recording materials which are typically described In Japanese Patent Publication No. 20144/1967, etc. are used in such fields as vouchers and printers on computers. Thermal recording materials which are typically described in Japanese Patent Publication No. 14039/1970, etc. have a broad range of applications including recorders for instrumentation, facsimile, printers and automatic ticket vending machines.

Such recording materials are required to exhibit high performance in various respects including whiteness of background, storage stability of the background, color rendition, sensitivity for color formation, initial color density and storage stability of a color image, and it is essential to use color formers that specifically suit these purposes. Color formers for use with pressure-sensitive recording materials must satisfy an additional important characteristic requirement for high solubility in inner-phase solvent(s) (capsule oil(s)). Fluoran compounds are extensively used as color formers with various types of conventional recording materials.

While many compounds have already been known as fluoran compounds, those which have structural formulas similar to the structural chemical formula [formula (1)] corresponding to the crystal modification of fluoran according to the present invention include the following three known types: fluorans of formulas (2), (3) and (4) as described in Japanese Patent Publication Nos. 32767/1974 and 17490/1974; fluoran of formula (5) as described in Japanese Patent Public Disclosure (Laid-Open) No. 123556/1985; and fluoran of formula (6) as described in Japanese Patent Public Disclosure (Laid-Open) No. 283183/1989. For the respective formulas (1)–(6), see below:

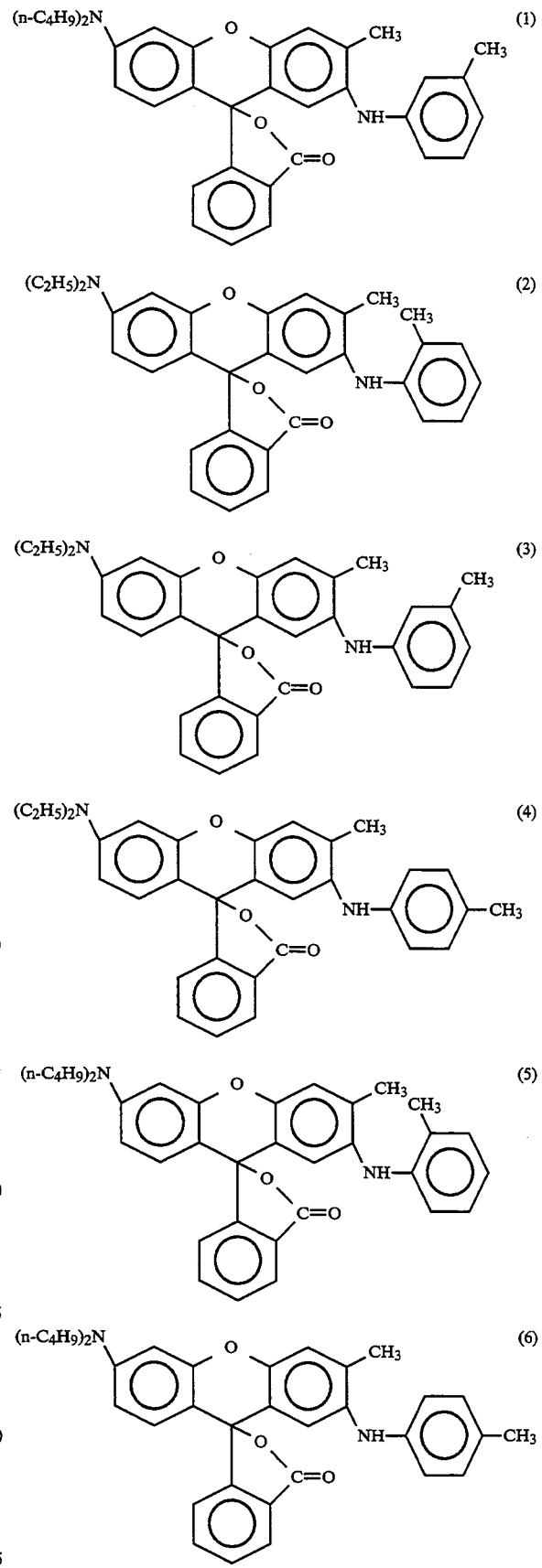

The fluoran of formula (2), however, has the problem that it has too low a solubility in inner-phase solvent(s)

to be effectively used as a color former in pressure-sensitive recording materials. Pressure-sensitive recording materials using this fluoran exhibit low whiteness and lightfastness of the CB surface and the color image formed on those materials is also low in lightfastness. Thermal recording materials using the fluoran (2) are low not only in the lightfastness of the background but also in the dynamic sensitivity for color formation and the storage stability of the color image formed on those materials. As a further problem, if the fluoran under consideration is used in common pressure-sensitive recording materials which use a zinc salt of a salicylic acid derivative as a color developer (which recording materials are hereunder referred to as "conventional pressure-sensitive recording materials") and in common thermal recording materials which use bisphenol A as a color developer (which recording materials are hereunder referred to as "conventional thermal recording materials"), the color rendered is purplish black and additional toning is necessary to attain a pure black color.

The fluoran of formula (3) has the problem that its solubility in inner-phase solvent(s) is insufficient to justify its use as a color former in pressure-sensitive recording materials. Pressure-sensitive recording materials using this fluoran are low in the whiteness of the CB surface and its lightfastness is also insufficient. Thermal recording materials using the fluoran (3) exhibit not only low background whiteness but also insufficient storage stability of the color image formed on those materials.

The fluoran of formula (4) has the problem that it has too low a solubility in inner-phase solvent(s) to be effectively used as a color former in pressure-sensitive recording materials. Pressure-sensitive recording materials using this fluoran exhibit not only low whiteness of the CB surface but also insufficient lightfastness; in addition, the color image formed on those materials is low in lightfastness. Thermal recording materials using the fluoran (4) exhibit not only low whiteness and lightfastness of the background but also poor dynamic sensitivity for color formation; in addition, the storage stability of the color image formed on those materials is by no means sufficient. As a further problem, if the fluoran under consideration is used in conventional pressure-sensitive and thermal recording materials, the color rendered is greenish black and additional toning is necessary to attain a pure black color.

The fluoran of formula (5) is also insufficient in solubility in inner-phase solvent(s). A pressure-sensitive recording material using this fluoran exhibits low whiteness and lightfastness of the CB surface; in addition, the color image formed on those materials also exhibits low lightfastness. Thermal recording materials using the fluoran (5) exhibit not only low whiteness and lightfastness of the background but also poor dynamic sensitivity for color formation and insufficient storage stability of the color image formed on those materials. As a further problem, if the fluoran under consideration is used in conventional pressure-sensitive and thermal recording materials, the color rendered is reddish black and additional toning is necessary to attain a pure black color.

The fluoran of formula (6) also exhibits insufficient solubility in inner-phase solvent(s). Pressure-sensitive recording materials using this fluoran also exhibit insufficient lightfastness of the CB surface; in addition, the color image formed on those materials has only low lightfastness. Thermal recording materials using the fluoran (6) exhibit not only low whiteness and storage stability of the background but also poor dynamic sensitivity for color formation; in addition, the storage stability of the color image formed on those recording materials is insufficient. Further, if the fluoran under consideration is used in conventional pressure-sensitive and thermal recording materials, the color rendered is greenish black and additional toning is necessary to attain a pure black color.

SUMMARY OF THE INVENTION

An object, therefore, of the present invention is to provide crystal modifications or a crystalline toluene adduct of a fluoran compound that are satisfactory in each of the characteristics to be possessed by color formers for use in various kinds of recording materials.

Another object of the present invention is to provide a process for producing those crystal modifications and a crystalline toluene adduct of a fluoran compound.

These objects of the present invention can be attained by using crystal modifications and/or a crystalline toluene adduct of 2-m-toluidino-3-methyl-6-di-n-butylaminofluoran.

As a result of intensive studies conducted in order to attain the above-stated objects, the present inventors found that two types of crystal modifications and one crystalline toluene adduct existed with 2-m-toluidino-3-methyl-6-di-n-butylaminofluoran and that those crystal modifications and crystalline toluene adduct had satisfactory characteristics for use as color formers in various kinds of recording materials.

In its first aspect, the present invention relates to a crystal modification of 2-m-toluidino-3-methyl-6-di-n-butylaminofluoran that is characterized by characteristic peaks at diffraction angles ($2\theta \pm 0.2°$) of 8.4°, 9.8°, 17.7°, 21.0° and 22.8° on X-ray diffractiometry using Cu-K$\alpha$ rays (which modification is hereunder referred to as "$\alpha$-type crystal modification").

The present invention also relates to a crystal modification of 2-m-toluidino-3-methyl-6-di-n-butylaminofluoran that is characterized by characteristic peaks at diffraction angles ($2\theta \pm 0.2°$) of 11.7°, 14.4°, 16.4°, 19.2° and 21.3° on X-ray diffractiometry using Cu-K$\alpha$ rays (which modification is hereunder referred to as "$\beta$-type crystal modification").

The present invention further relates to a crystalline toluene adduct of 2-m-toluidino-3-methyl-6-di-n-butylaminofluoran that is characterized by characteristic peaks at diffraction angles ($2\theta \pm 0.2°$) of 5.6°, 9.2°, 11.0°, 16.2°, 18.0° and 23.1° on X-ray diffractiometry using Cu-K$\alpha$ rays (which adduct is hereunder referred to as a "toluene adduct").

In its second aspect, the present invention relates to recording materials that contain those crystal modifications and/or a toluene adduct as color formers.

In its third aspect, the present invention relates to a process for producing the $\alpha$-type crystal modification by treating the toluene adduct in methanol at 0°–60° C.

The present invention also relates to a process for producing the $\beta$-type crystal modification by recrystallizing the $\alpha$-type crystal modification and/or the toluene adduct with at least one solvent selected from among ethanol, isopropyl alcohol, n-butanol and acetonitrile.

The present invention further relates to a process for producing the $\beta$-type crystal modification by dispersing the $\alpha$-type crystal modification and/or the toluene adduct in at least one solvent selected from among ethanol, isopropyl alcohol and n-butanol and treating the dispersion at a temperature ranging from room temperature to the reflux temperature.

The present invention also relates to a process for producing the β-type crystal modification by treating the toluene adduct at a temperature of 30°–110° C. under vacuum.

The present invention further relates to a process for producing the toluene adduct by precipitating a crystal from a toluene solution of 2-m-toluidino-3-methyl-6-di-n-butylaminofluoran.

DETAILED DESCRIPTION OF THE PREFERRED EMBODIMENTS

Figure 1:
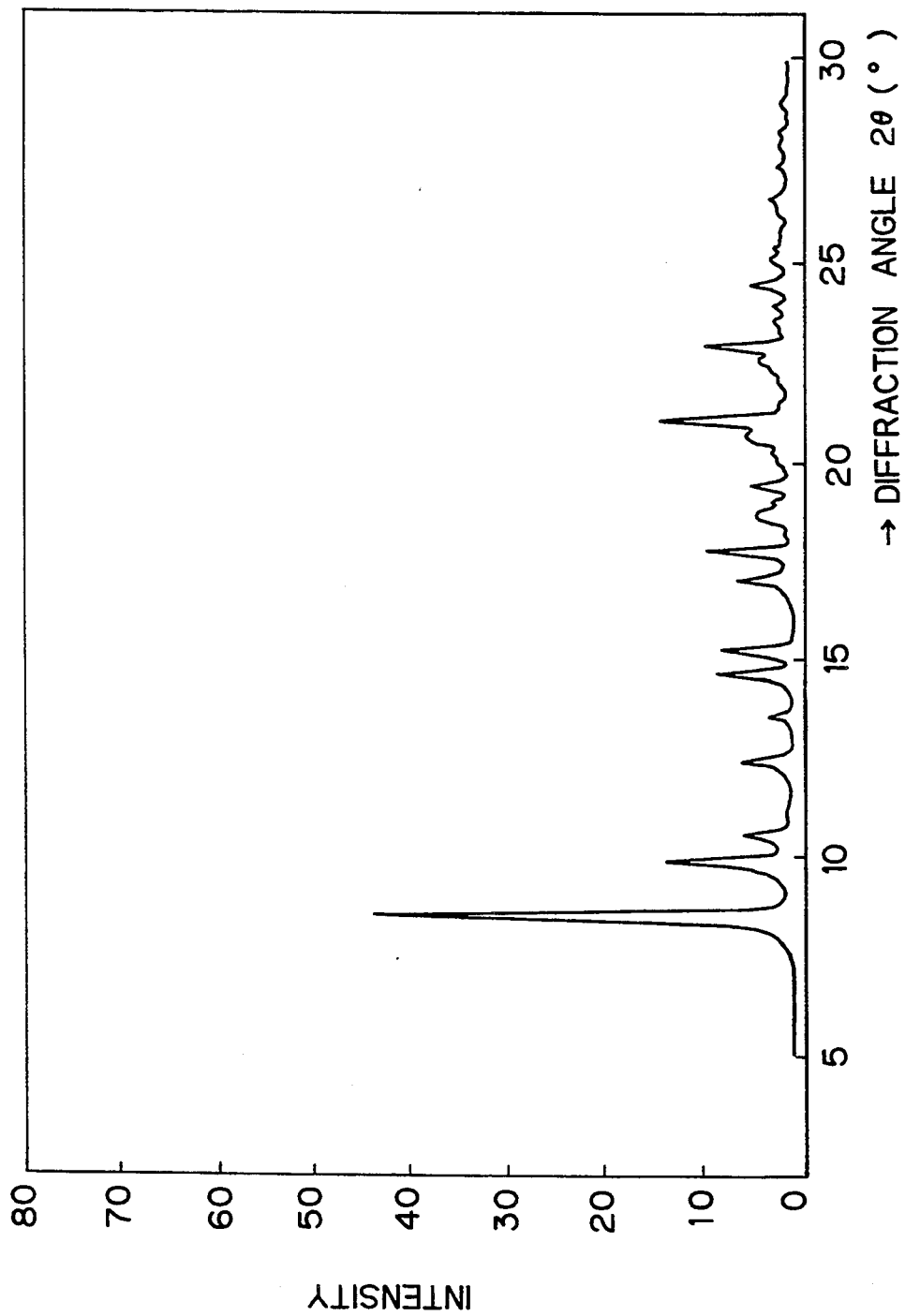
FIG. 1 is a X-ray diffraction diagram for the α-type crystal modification of 2-m-toluidino-3-methyl-6-di-n-butylaminofluoran as produced in Example 1.

The α-type crystal modification, β-type crystal modification and toluene adduct described hereinabove provide different X-ray diffraction patterns and melting points.

The α-type crystal modification, β-type crystal modification and toluene adduct under consideration have high solubility in inner-phase solvent(s) for use with pressure-sensitive recording materials, such as commonly employed SAS-296 (Nippon Oil Co., Ltd.) and KMC-113 (Kureha Chemical Industry Co., Ltd.) and, hence, pressure-sensitive recording materials that used those compounds as color formers exhibited high whiteness and lightfastness of the CB surface and could produce a pure black color, with the resulting color image exhibiting satisfactory storage stability.

When the α-type or β-type crystal modification was used as a color former in thermal recording materials, the background exhibited high levels of whiteness and storage stability; at the same time, the recording materials had high dynamic sensitivity for color formation and could produce a pure black color, with the resulting color image exhibiting satisfactory storage stability.

Surprisingly, those features of the crystal modifications and toluene adduct were absent from fluoran compounds having similar structures, in particular, the fluoran of formula (5) having a 2-o-toluidino group and the fluoran of formula (6) having a 2-p-toluidino group.

Thus, the α-type crystal modification, β-type crystal modification and toluene adduct of 2-m-toluidino-3-methyl-6-di-n-butylaminofluoran according to the present invention are very useful as color formers in recording materials, in particular, pressure-sensitive recording materials and thermal recording materials.

The two types of crystal modification of 2-m-toluidino-3-methyl-6-di-n-butylaminofluoran, as well as its toluene adduct may be produced by the following process:

A benzophenone compound represented by formula (I):

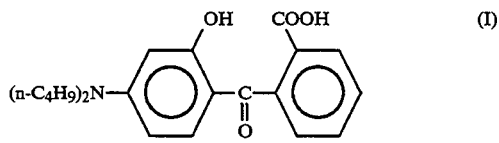

is reacted with a diphenylamine compound of formula (II)

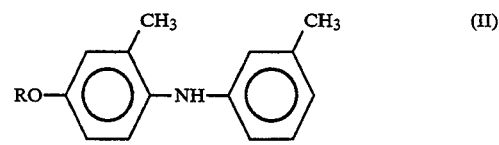

(where R is a lower alkyl group) in the presence of a dehydrating/condensing agent at a temperature of 0°–100° C. for a period of from several hours to less than a hundred hours, and the reaction product is treated with an alkali.

Exemplary dehydrating/condensing agents that can be used include conc. sulfuric acid, fuming sulfuric acid, poly(phosphoric acid), phosphorus pentoxide, etc. and conc. sulfuric acid is particularly preferred. If conc. sulfuric acid is to be used as a dehydrating/condensing agent, the reaction temperature is preferably in the range of 0°–50° C. The treatment with an alkali is such that the product of reaction between the two starting materials (I) and (II) in the presence of a dehydrating/condensing agent is placed under alkali conditions at a temperature in a specified range for a time period in a specified range. Exemplary alkalies that can be used include sodium hydroxide, potassium hydroxide and sodium carbonate, with sodium hydroxide being particularly preferred. If sodium hydroxide is to be used as an alkali, it is preferably used as an aqueous solution. Treatment with alkalies is conducted at a temperature of 0°–100° C., preferably 50°–100° C.; generally speaking, the efficiency of this treatment increases with temperature. Alkalies are preferably used in such amounts that the treating solution will have a pH of at least 9 or more.

The alkali-treated reaction product is then extracted with an organic solvent for purification. The organic solvent may already be present in the stage of alkali treatment. Exemplary organic solvents that can be used include benzene, toluene, xylene, chlorobenzene, etc. and toluene is customarily used with preference. In order to prepare the toluene adduct, toluene is used as an organic solvent or it is necessary to use an organic solvent that contains at least 5% of toluene. In the pages that follow, the case of preparing the toluene adduct with toluene being used as an organic solvent is described.

The toluene extract is concentrated until the residual toluene is reduced to a low level. Upon cooling, the crystal of the toluene adduct is precipitated. The precipitated crystal is recovered by filtration, washed with a small amount of cold toluene and dried, yielding the desired crystal of the toluene adduct.

In order to obtain the toluene adduct in high purity, the toluene extract is preferably concentrated in such a way that the residual toluene content is at least equal to the weight of the compound of formula (I). If the toluene extract is concentrated to such an extent that the residual toluene content is less than the weight of the compound (I), a β-type crystal modification may occasionally accompany the precipitated crystal of the toluene adduct.

If desired, the α-type crystal modification, β-type crystal modification or the crystal of the toluene adduct into which those crystal modifications have been introduced may be dissolved in toluene, followed by reprecipitation to achieve conversion to the toluene adduct of higher purity. In this case, toluene is used in an amount 3–20 times, preferably 4–15 times, the weight of either type of crystal modification or the toluene adduct into which they have been introduced. After the crystal is completely dissolved in toluene, optionally assisted by heating, the solution is concentrated to such a state that the residual toluene content is at least equal to the weight of the crystal used and, by optional cooling, the crystal will be precipitated. The precipitating crystal is recovered by filtration, washed with a small amount of cold toluene and dried, thereby yielding the desired toluene adduct in high purity.

The toluene adduct has a melting point of about 112°–119° C. and shows characteristic peaks at diffraction angles ($2\theta \pm 0.2°$) of 5.6°, 9.2°, 11.0°, 16.2°, 18.0° and 23.1° on X-ray diffractiometry using Cu-Kα rays.

On the basis of the result of analysis of $^1$H-NMR spectra and by elemental analysis, it is speculated that the toluene adduct under consideration is a crystal composed of 2 moles of 2-m-toluidino-3-methyl-6-di-n-butylaminofluoran and 1 mole of toluene.

The α-type crystal modification can be prepared consistently by treating the toluene adduct with methanol. The treatment with methanol is such that the toluene adduct is mixed with methanol, preferably under agitation. For this treatment, methanol is used in an amount 2–20 times, preferably 4–15 times, the weight of the toluene adduct. Depending on the temperature for the treatment, conversion to the α-type crystal modification will not proceed if the amount of methanol used is less than twice the weight of the toluene adduct; if the amount of methanol used exceeds 20 times the weight of the toluene adduct, the β-type crystal modification tends to accompany the α-type crystal modification being produced.

The temperature for the methanol treatment is in the range of 0°–60° C., preferably 0°–45° C. If the treatment temperature is lower than 0° C., the period of treatment is simply prolonged without any compensatory merit. If the treatment temperature is higher than 60° C., the β-type crystal modification is likely to accompany the α-type crystal modification being prepared.

The time taken for the methanol treatment is in the range of 10 min–24 h, preferably 20 min–15 h. The treatment is preferably conducted under agitation.

The α-type crystal modification can be prepared from crystalline solvent adducts other than the toluene adduct, such as a crystalline monochlorobenzene adduct, by a similar procedure to that adopted for treating the toluene adduct. However, from a commercial production viewpoint including such aspects as cost and safety, the use of the toluene adduct is preferred.

The α-type crystal modification has a melting point of about 135°–141° C. and shows characteristic peaks at diffraction angles ($2\theta \pm 0.2°$) of 8.4°, 9.8°, 17.7°, 21.0° and 22.8° on X-ray diffractiometry using Cu-Kα rays.

The β-type crystal modification can be produced consistently by recrystallizing the α-type crystal modification and/or the toluene adduct with a specified organic solvent, say, at least one solvent selected from among ethanol, isopropyl alcohol, n-butanol and acetonitrile.

The amount of organic solvent to be used for recrystallization will vary with its type but, preferably, it is used in a minimum amount that completely dissolves the α-type crystal modification and/or toluene adduct of interest at the reflux temperature, with the complete solution being subsequently cooled to precipitate the crystal.

The β-type crystal modification can also be prepared using an excess amount of the solvent described above to make a complete solution of the α-type crystal modification and/or toluene adduct, which is then concentrated to a predetermined amount. Even if the solvent is not used in an amount that permits the α-type crystal modification and/or toluene adduct to be completely dissolved, the β-type crystal modification can also be obtained by dispersing them in a given amount of solvent and treating the dispersion at a given temperature. The term "treating" as used herein means mixing the α-type crystal modification and/or toluene adduct with a solvent, preferably under agitation.

The amount of solvent to be used varies with its type but the lower limit is such that the crystal can be thoroughly dispersed and agitated whereas the upper limit is such that the crystal will not be completely dissolved at the temperature for treatment. To take ethanol as an example, it is used in an amount 1–20 times, preferably 3–15 times, the weight of the α-type crystal modification and/or toluene adduct.

The temperature for the treatment is in the range of from room temperature to the reflux temperature, preferably ranging from 40° C. to the reflux temperature. Below room temperature, the crystal conversion is very much retarded.

The treatment time is in the range of 10 min–24 h, preferably 20 min–15 h. The treatment is preferably conducted under agitation.

The β-type crystal modification may also be obtained by heat-treating the toluene adduct under vacuum. The heat treatment under vacuum is such that the toluene adduct is placed under the conditions just described below. The pressure to be applied is in the range of 0–200 mmHg, preferably 1–100 mmHg. The heating temperature is in the range of 20°–110° C., preferably 60°–105° C. The treatment may be conducted as the toluene adduct is left to stand; alternatively, it may be subjected to a mixing action such as agitation.

The β-type crystal modification has a melting point of about 143°–148° C. and shows characteristic peaks at diffraction angles ($2\theta \pm 0.2°$) of 11.7°, 14.4°, 16.4°, 19.2° and 21.3° on X-ray diffractiometry using Cu-Kα rays.

The α-type crystal modification, β-type crystal modification and toluene adduct of 2-m-toluidino-3-methyl-6-di-n-butylaminofluoran prepared in accordance with the present invention may be used, either individually or as admixtures, in various kinds of recording materials. If necessary, they may be used in combination with other color formers.

Any color formers that are commonly used in recording materials of the types contemplated by the present invention may be used in combination with the α-type crystal modification, β-type crystal modification or toluene adduct described above. Particularly preferred color formers are those which are based on triphenylmethanephthalide, fluoran, fluorene, vinylogphthalide, etc. As specific examples, the following may be mentioned: 3,3-bis(p-dimethylaminophenyl)-6-dimethylaminophthalide; 2-anilino-3-methyl-6-dimethylaminofluoran; 2-anilino-3-methyl-6-diethylaminofluoran; 2-anilino-3-methyl-6-dipropylaminofluoran; 2-anilino-3-methyl-6-dibutylaminofluoran; 2-anilino-3-methyl-6-dipentylaminofluoran; 2-anilino-3-methyl-6-(N-methyl-N-propylamino)fluoran; 2-anilino-3-methyl-6-(N-ethyl-N-isobutylamino)fluoran; 2-anilino-3-methyl-6-(N-ethyl-N-isopentylamino)fluoran; 2-anilino-3-methyl-6-(N-methyl-N-cyclohexylamino)fluoran; 2-anilino-3-methyl-6-(N-ethyl-N-tetrahydrofurfurylamino)fluoran; 3,6-bis(dimethylamino)fluorenespiro[9,3']-6'-dimethylaminophthalide; 3,3-bis{2,2-bis(p-dimethylaminophenyl)ethenyl}-4,5,6,7-tetrachlorophthalide; 3,3-bis{2,2-bis(1-ethyl-2-methylindol-3-yl)ethenyl}-4,5,6,7-tetrachlorophthalide; etc. These color formers may be used either individually or as admixtures.

The α-type crystal modification, β-type crystal modification and/or toluene adduct of the present invention may be applied to pressure-sensitive recording materials by various known methods such as the one described in Japanese Patent Publication No. 20144/1967, etc. A typical method is as follows: a solution of a color former in an inner-phase solvent(s) is encapsulated with a polymeric compound being used as a membrane forming material; the dispersion of the capsule is coated on the back side of a base such as a wood-free paper, synthetic paper or plastic film to make an upper leaf; in a separate step, a color developer is coated on the obverse surface of another base to make a lower leaf; the upper and the lower leaf are superposed in such a way that their coated surfaces contact each other, when a pressure is exerted such as by writing or striking, the capsules in the area under pressure are disrupted, whereupon the color former in the capsules reacts with the color developer to form a recorded image on the surface of the lower leaf. More than one copy can be obtained by inserting between the upper and the lower leaf a plurality of intermediate leaves each comprising a base that has a color developer and capsules coated on the obverse and reverse surfaces, respectively.

The present invention is also applicable to other kinds of pressure-sensitive materials such as paper of a "self-contained" type which has both a color developer and capsules formed on the same side of a base, and a system in which either one of the color developer or the capsules is contained in a base whereas the other is coated on the base.

Examples of the color developer that can be used in pressure-sensitive materials include acid clay, zinc salts of salicylic acid derivatives, a zinc salt of p-octylphenol resin, p-phenylphenol resin, etc. Among these color developers, zinc salts of salicylic acid derivatives and a zinc salt of p-octylphenol resin are used with particular preference.

The α-type crystal modification and β-type crystal modification of the present invention may be applied to thermal recording materials by various known methods such as the one described in Japanese Patent Publication No. 14039/1970, etc. In a typical method, a color former, a color developer and a sensitizer are each dispersed in an aqueous solution of a water-soluble polymer such as poly(vinyl alcohol) by means of an attritor, a sand mill or the like until the particle size of each reagent is reduced to less than ten microns. The sensitizer may be added to either one or both of the color former and the color developer, so that they are dispersed simultaneously. If desired, the sensitizer may be dispersed as a preliminarily formed eutectic with the color former or the color developer. The thus prepared dispersions of the respective components are mixed together and any necessary ingredients such as a pigment, a binder, a wax, a metal soap, an antioxidant and a uv absorber are added so as to prepare a heat-sensitive coating dispersion. The coating dispersion is applied to a base such as wood-free paper, synthetic paper or plastic film and calendered to impart smoothness, whereby a desired thermal recording material is obtained. Depending on the necessity for providing improved color forming properties, the heat-sensitive coating dispersion may be applied onto a base having a precoat of heat-insulating layer of plastic pigment or silica, etc. Furthermore, if it is necessary to impart resistance to water and chemicals, a topcoat may be formed on the thermal recording layer using an aqueous solution of a water-soluble polymer, etc.

Various kinds of phenolic compounds may be used as color developers in thermal recording materials. Specific examples include: 2,2-bis(p-hydroxyphenyl)propane (commonly known as "bisphenol A"), 2,2-bis(p-hydroxyphenyl)-4-methylpentane; 1,1-bis(p-hydroxyphenyl)cyclohexane; bis(p-hydroxyphenyl) sulfone (commonly known as "bisphenol S"); bisphenol S monoisopropyl ether; 3,3'-diallylbisphenol S; 1,5-bis(p-hydroxyphenylmercapto)-3-oxapentane; benzyl p-hydroxybenzoate; tetrabromobisphenol A and tetrabromobisphenol S. Among these phenolic compounds, bisphenol A may be used with particular preference.

Exemplary sensitizers include: p-benzylbiphenyl; m-terphenyl; 2-benzyloxynaphthalene; 1,4-dibenzyloxy naphthalene; dibenzyl oxalate; di-(p-methylbenzyl) oxalate; 1,2-diphenoxyethane; 1,2-di-m-toluoxyethane; 1,2-di-p-toluoxyethane; 1,4-diphenoxybutane; benzyl p-benzyloxybenzoate; phenyl 2-naphthoate; phenyl 1-hydroxy-2-naphthoate; dibenzyl terephthalate; etc. Among these sensitizers, p-benzylbiphenyl; m-terphenyl; 2-benzyloxynaphthalene; di-(p-methylbenzyl oxalate) and 1,2-di-m-toluoxyethane may be used with particular preference.

The pigments that can be used may be organic or inorganic. Specific examples of preferred pigments include calcium carbonate, barium sulfate, titanium oxide, aluminum hydroxide, amorphous silica, urea-formaldehyde resin (powders) and polyethylene resin powders.

The binders that can be used are water-soluble polymers and water-insoluble polymers. Specific examples of water-soluble polymers as preferred binders include: methyl cellulose, carboxymethyl cellulose, hydroxyethyl cellulose, starches, styrene-maleic anhydride copolymer hydrolyzate, ethylene-maleic anhydride copolymer hydrolyzate, isobutylene-maleic anhydride copolymer hydrolyzate, poly(vinyl alcohol), carboxy-modified poly(vinyl alcohol) and polyacrylamide. Specific examples of water-insoluble polymers as preferred binders include: styrene-butadiene rubber latex, acrylonitrile-butadiene rubber latex, and vinyl acetate emulsions.

Specific examples of preferred waxes include paraffin wax, carboxy-modified paraffin wax and polyethylene wax.

Metal salts of higher aliphatic acids may be used as metal soaps and specific examples of preferred metal soaps include zinc stearate, calcium stearate and aluminum stearate.

Hindered phenols may be used as antioxidants. Ultraviolet absorbers that can be used are those which are based on benzophenone and benzotriazole.

The following examples are provided for the purpose of further illustrating the present invention but are in no way to be taken as limiting.

EXAMPLE 1

Production of the α-type Crystal Modification of 2-m-toluidino-3-methyl-6-di-n-butylaminofluoran To 100 ml of 98% sulfuric acid, 37.0 g of 2-(2-hydroxy-4-di-n-butylaminobenzoyl)benzoic acid was added in small portions at 25° C. or below to give a complete solution. Thereafter, 25.0 g of 2,3'-dimethyl-4-methoxydiphenylamine was added dropwise at 10°-20° C. The mixture was stirred at room temperature for 20 h and the reaction product was discharged into 1000 g of ice water. The resulting precipitate was recovered by filtration and refluxed under agitation for 1 h together with 200 ml of toluene and 130 ml of an aqueous solution of 25% sodium hydroxide.

Figure 4:
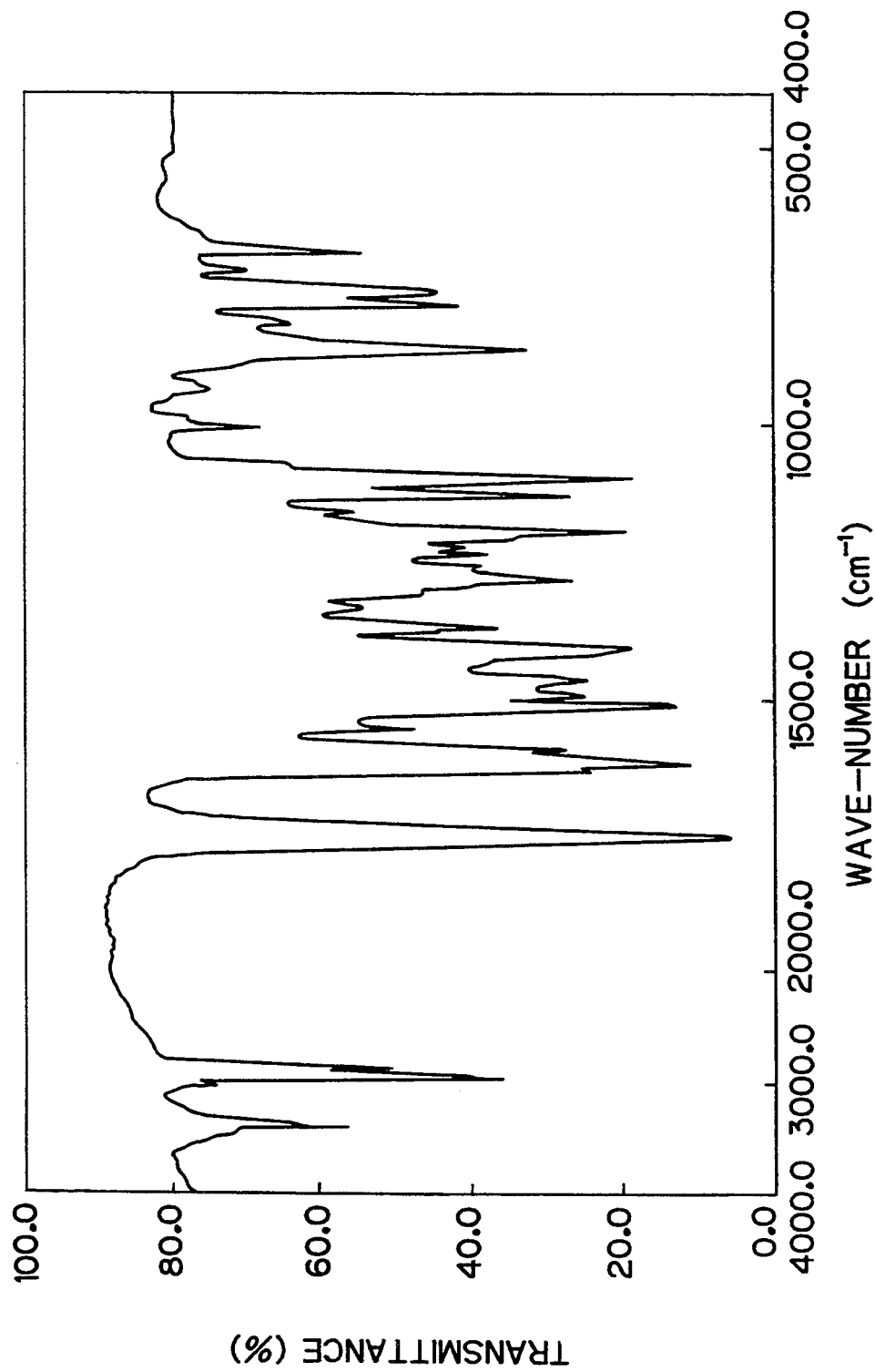
FIG. 4 is an infrared absorption spectrum of the α-type crystal modification of 2-m-toluidino-3-methyl-6-di-n-butylaminofluoran as produced in Example 1.

Subsequently, the toluene layer was separated out and washed with warm water. After toluene being distilled off under vacuum, 100 ml of methanol was added and the mixture was stirred at 40° C. for 1 h, followed by cooling. The resulting crystal was recovered by filtration and dried to produce a pale yellowish white crystal in an amount of 4.8 g (yield: 82.0%). The melting point of the crystal, as well as its elemental analysis, parent peak of mass analysis and characteristic absorption of IR absorption spectrum were as listed below. A X-ray diffraction diagram for the crystal is shown in FIG. 1 and its IR absorption spectrum in FIG. 4. m.p. 138°-140° C.

| Elemental analysis for $C_{36}H_{38}N_2O_3$ | C | H | N |
|---|---|---|---|
| Cal'd: | 79.09% | 7.01% | 5.13 |
| Found: | 78.96% | 6.99% | 5.13% |

MS (m/e): 546 (M+) IR: υNH 3400 cm$^{-1}$

EXAMPLE 2

Production of the α-type Crystal Modification of 2-m-toluidino-3-methyl-6-di-n-butylaminofluoran The same materials as used in Example 1 were subjected to the same reaction and the reaction product was similarly treated with toluene and sodium hydroxide.

Subsequently, the toluene layer was separated out and washed with warm water. Thereafter, toluene was distilled off under vacuum until the residue weighed about 100 g and the precipitated crystal was recovered by filtration. To the recovered crystal, 100 ml of methanol was added and the mixture was stirred at 40° C. for 1 h, followed by cooling. The resulting crystal was recovered by filtration and dried to produce a pale yellowish white crystal in an amount of 43.1 g (yield: 78.9%). The melting point of the crystal, as well as its X-ray diffraction diagram, mass spectrum and IR absorption spectrum were the same as those of the crystal obtained in Example 1.

EXAMPLE 3

Production of the β-type Crystal Modification of 2-m-toluidino-3-methyl-6-di-n-butylaminofluoran The same materials as used in Example 1 were subjected to the same reaction and the reaction product was similarly treated with toluene and sodium hydroxide.

Figure 2:
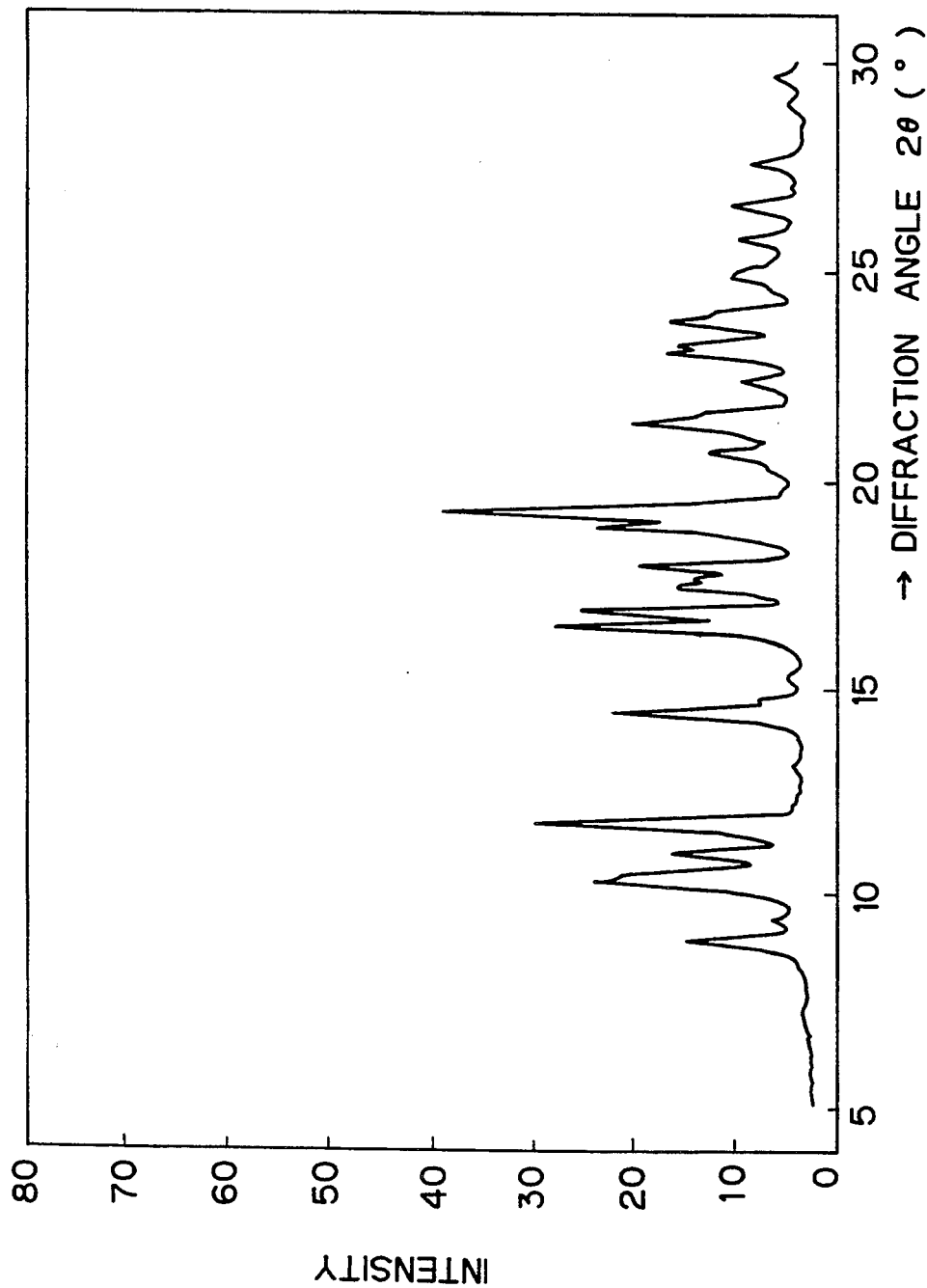
FIG. 2 is a X-ray diffraction diagram for the β-type crystal modification of 2-m-toluidino-3-methyl-6-di-n-butylaminofluoran as produced in Example 3.
Figure 5:
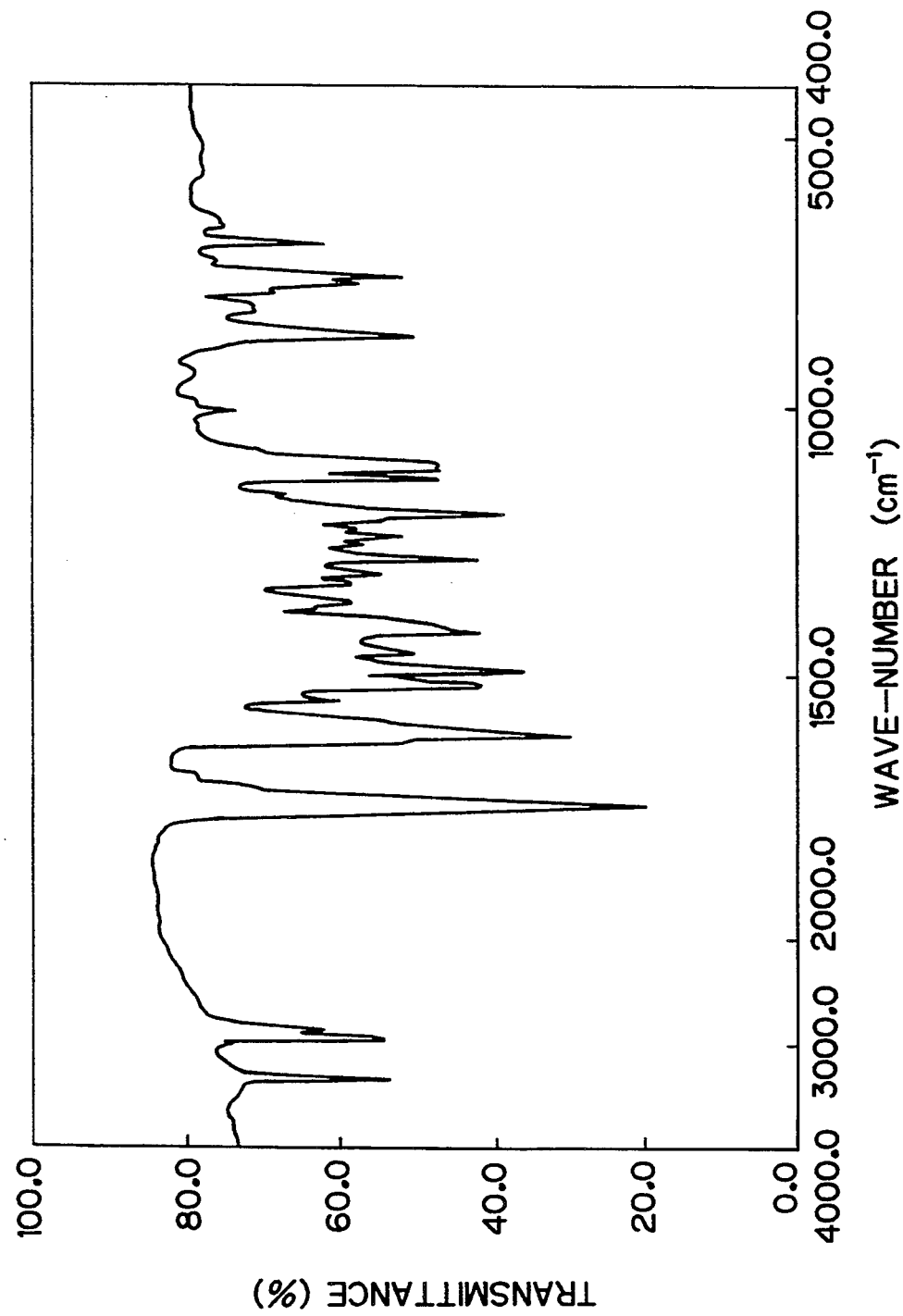
FIG. 5 is an infrared absorption spectrum of the β-type crystal modification of 2-m-toluidino-3-methyl-6-di-n-butylaminofluoran as produced in Example 3.

The toluene extract was washed with warm water and toluene was distilled off to produce the residue in an amount of 55.8 g. The residue was recrystallized from 560 ml of isopropyl alcohol, producing a pale yellowish white crystal in an amount of 45.7 g (yield: 83.7%). The melting-point of the crystal, as well as its elemental analysis, parent peak of mass analysis and characteristic absorption of IR absorption spectrum were as listed below. A X-ray diffraction diagram for the crystal is shown in FIG. 2 and its IR absorption spectrum in FIG. 5. m.p. 145°-147° C.

| Elemental analysis for $C_{36}H_{38}N_2O_3$ | C | H | N |
|---|---|---|---|
| Cal'd: | 79.09% | 7.01% | 5.13% |
| Found: | 79.15% | 7.03% | 5.15% |

MS (m/e): 546 (M+) IR: υNH 3350 cm$^{-1}$

EXAMPLE 4

Production of the β-type Crystal Modification of 2-m-toluidino-3-methyl-6-di-n-butylaminofluoran The procedure of Example 3 was repeated except that isopropyl alcohol used as a recrystallizing solvent was replaced by ethanol. A crystal was obtained in an amount of 46.6 g (yield: 85.3%). The appearance of the crystal, as well as its X-ray diffraction diagram, melting point, mass spectrum and IR absorption spectrum were the same as those of the crystal obtained in Example 3.

EXAMPLE 5

Production of the β-type Crystal Modification of 2-m-toluidino-3-methyl-6-di-n-butylaminofluoran The procedure of Example 3 was repeated except that isopropyl alcohol used as a recrystallizing solvent was replaced by n-butanol. A crystal was obtained in an amount of 43.6 g (yield: 79.8%). The appearance of the crystal, as well as its X-ray diffraction diagram, melting point, mass spectrum and IR absorption spectrum were the same as those of the crystal obtained in Example 3.

EXAMPLE 6

Production of the β-type Crystal Modification of 2-m-toluidino-3-methyl-6-di-n-butylaminofluoran The procedure of Example 3 was repeated except that isopropyl alcohol used as a recrystallizing solvent was replaced by acetonitrile. A crystal was obtained in an amount of 39.4 g (yield: 72.1%). The appearance of the crystal, as well as its X-ray diffraction diagram, melting point, mass spectrum and IR absorption spectrum were the same as those of the crystal obtained in Example 3.

EXAMPLE 7

Production of the Crystalline Toluene Adduct of 2-m-toluidino-3-methyl-6-di-n-butylaminofluoran The same materials as used in Example 1 were subjected to the same reaction and the reaction product was similarly treated with toluene and sodium hydroxide.

Figure 3:
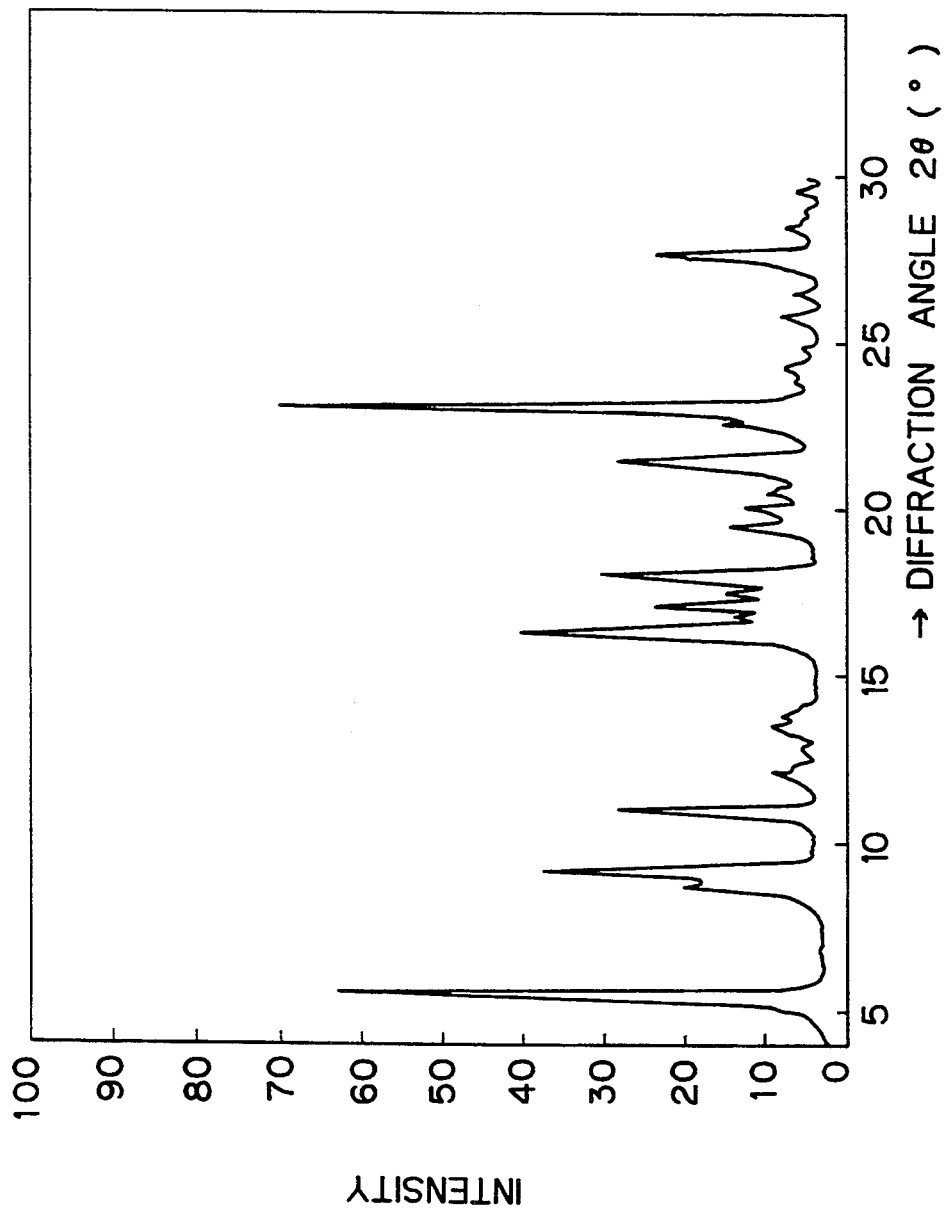
FIG. 3 is a X-ray diffraction diagram for the crystalline toluene adduct of 2-m-toluidino-3-methyl-6-di-n-butylaminofluoran as produced in Example 7.
Figure 6:
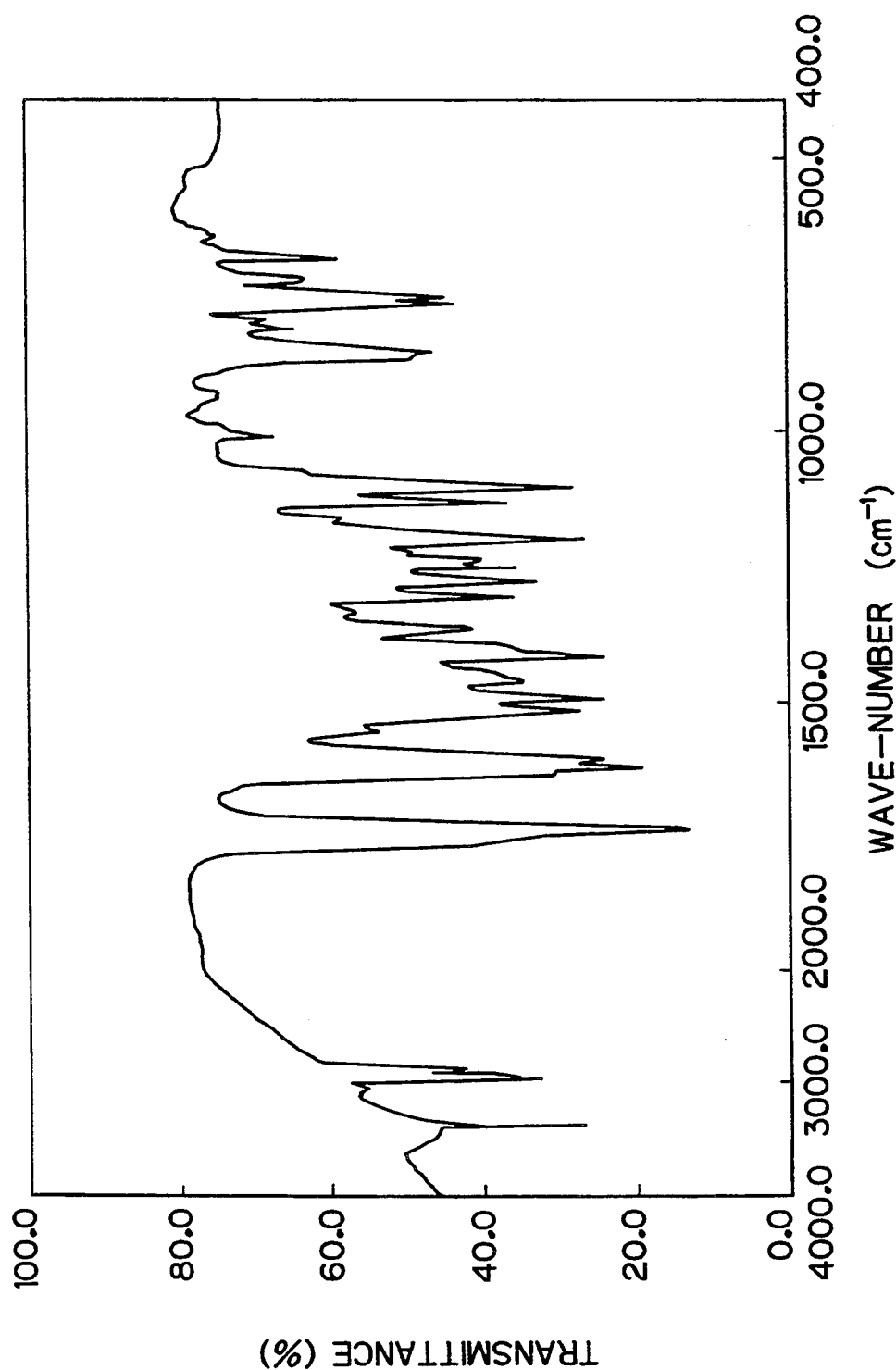
FIG. 6 is an infrared absorption spectrum of the crystalline toluene adduct of 2-m-toluidino-3-methyl-6-di-n-butylaminofluoran as produced in Example 7.

The toluene extract was washed with warm water and toluene was concentrated under vacuum until the residue weighed about 100 g. By subsequent cooling, a crystal was precipitated. The crystal was recovered by filtration, washed with a small amount of cold toluene and dried to produce a pale yellowish white crystal in an amount of 49.2 g (yield: 83.0%). The melting point of the crystal, as well as its elemental analysis and characteristic absorption of IR absorption spectrum were as listed below. A X-ray diffraction diagram for the crystal is shown in FIG. 3 and its IR absorption spectrum in FIG. 6. m.p. 113°–117° C.

| Elemental analysis for $2C_{36}H_{38}N_2O_3 \cdot C_7H_8$ | C | H | N |
| --- | --- | --- | --- |
| Cal'd: | 80.03% | 7.14% | 4.73% |
| Found: | 80.43% | 7.24% | 4.76% |

IR: $\nu$NH 3385 cm$^{-1}$

EXAMPLE 8

Production of the Crystalline Toluene Adduct of 2-m-toluidino-3-methyl-6-di-n-butylaminofluoran The β-type crystal modification (50.0 g) of 2-m-toluidino-3-methyl-6-di-n-butylaminofluoran was dispersed in 500 ml of toluene and the dispersion was heated at 60° C. to make a solution. Thereafter, toluene was concentrated under vacuum until the residue weighed about 100 g. After cooling, the residue was left to stand in a water bath for 1 h and the precipitated crystal was recovered by filtration, washed with a small amount of cold toluene and dried to yield a crystal in an amount of 46.4 g. The appearance of the crystal, as well as its melting point, IR absorption spectrum and X-ray diffraction diagram were the same as those of the crystal obtained in Example 7.

EXAMPLE 9

Production of the α-type Crystal Modification of 2-m-toluidino-3-methyl-6-di-n-butylaminofluoran The crystalline toluene adduct (10.0 g) of 2-m-toluidino-3-methyl-6-di-n-butylaminofluoran as obtained in Example 7 was dispersed in 60 ml of methanol and the dispersion was stirred at 38°–41° C. for 30 min. The dispersion was then cooled in a water bath for 1 h and the resulting crystal was recovered by filtration and dried to give a weight of 8.9 g. The appearance of the crystal, as well as its X-ray diffraction diagram, melting point, mass spectrum and IR absorption spectrum were the same as those of the crystal obtained in Example 1.

EXAMPLE 10

Production of the α-type Crystal Modification of 2-m-toluidino-3-methyl-6-di-n-butylaminofluoran The crystalline toluene adduct (10.0 g) of 2-m-toluidino-3-methyl-6-di-n-butylaminofluoran as obtained in Example 7 was dispersed in 60 ml of methanol and the dispersion was stirred at room temperature for 15 h. The resulting crystal was recovered by filtration and dried to give a weight of 8.9 g. The appearance of the crystal, as well as its X-ray diffraction diagram, melting point, mass spectrum and IR absorption spectrum were the same as those of the crystal obtained in Example 1.

REFERENCE EXAMPLE 1

The crystalline toluene adduct (10.0 g) of 2-m-toluidino-3-methyl-6-di-n-butylaminofluoran as obtained in Example 7 was dispersed in 60 ml of methanol and the dispersion was stirred under reflux for 30 min. After cooling in a water bath for 1 h, the resulting crystal was recovered by filtration and dried to yield a pale yellowish white crystal in an amount of 8.7 g. As a result of identification by X-ray diffraction and thermal analysis (TG-DTA), the crystal was found to be a mixture of the α-type and β-type crystal modifications of the fluoran.

EXAMPLE 11

Production of the β-type Crystal Modification of 2-m-toluidino-3-methyl-6-di-n-butylaminofluoran The crystalline toluene adduct (10.0 g) of 2-m-toluidino-3-methyl-6-di-n-butylaminofluoran as obtained in Example 7 was dispersed in 60 ml of ethanol and the dispersion was stirred under reflux for 1 h. After cooling, the resulting crystal was recovered by filtration and dried to give a weight of 9.0 g. The appearance of the crystal, as well as its X-ray diffraction diagram, melting point, mass spectrum and IR absorption spectrum were the same as those of the crystal obtained in Example 3.

EXAMPLE 12

Production of the β-type Crystal Modification of 2-m-toluidino-3-methyl-6-di-n-butylaminofluoran The crystalline toluene adduct (20.0 g) of 2-m-toluidino-3-methyl-6-di-n-butylaminofluoran as obtained in Example 7 was treated by heating at 90° C. under a reduced pressure of 2–3 mmHg for 3 h, yielding a crystal in an amount of 18.4 g. The appearance of the crystal, as well as its X-ray diffraction diagram, melting point, mass spectrum and IR absorption spectrum were the same as those of the crystal obtained in Example 3.

EXAMPLE 13

Production of Pressure-Sensitive Recording Material

The α-type crystal modification (3 g) of 2-m-toluidino-3-methyl-6-di-n-butylaminofluoran as produced in Example 1 was dissolved in 47 g of KMC-113 (solvent available from Kureha Chemical Industry Co., Ltd.) under heating, thereby preparing a solution of the color former.

In a separate step, 5 g of an aqueous solution of 20% (specialty) anionic copolymer (available from Mitsui Toatsu Chemicals Inc. under the trade name "SM-100") was added to 100 g of water and the mixture was adjusted to a pH of 4 by adding an aqueous solution of sodium hydroxide. To the thus adjusted mixture, the solution of the color former (50 g) and a melamine-formaldehyde prepolymer (10 g) (available from Mitsui Toatsu Chemicals Inc. under the trade name "UMC-300") were added and the mixture was emulsified with a homo-mixer until the size of oil droplets was reduced to 4 microns. Subsequently, the emulsion was heated to 60° C. under agitation, which was continued for an additional one hour at the same temperature. After cooling to room temperature, the emulsion was adjusted to a pH of 7.5 with 25% aqueous ammonia for preparing a dispersion of encapsulated color former.

Ten grams of the thus prepared dispersion of encapsulated color former, 2 g of wheat starch and 1 g of a latex were mixed well and coated onto a sheet of wood-free paper to give a solids deposit of 5 g/m². The coating was dried to prepare an upper leaf.

EXAMPLE 14

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by the β-type crystal modification of 2-m-toluidino-3-methyl-6-di-n-butylaminofluoran as produced in Example 3.

EXAMPLE 15

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by the crystalline toluene adduct of 2-m-toluidino-3-methyl-6-di-n-butylaminofluoran as produced in Example 7.

EXAMPLE 16

Production of Thermal Recording Material

The α-type crystal modification (5 g) of 2-m-toluidino-3-methyl-6-di-n-butylaminofluoran as produced in Example 1 was pulverized to an average particle size of 1 micron in an aqueous solution (45 g) of 2.5% poly(vinyl alcohol) by means of a sand mill, whereby a dispersion of the color former was prepared.

In a separate step, 10 g of bisphenol A as a color developer and 10 g of p-benzylbiphenyl as a sensitizer were pulverized to an average particle size of 3 microns in an aqueous solution (80 g) of 2.5% poly(vinyl alcohol) by means of a sand mill, whereby a dispersion of the color developer was prepared.

The two dispersions were mixed together; to the mixture, a 50% dispersion of calcium carbonate (30 g) and a 30% dispersion of paraffin wax (15 g) were added and mixed well to form a heat-sensitive coating dispersion.

The thus prepared coating dispersion was applied to a sheet of wood-free paper to give a solids deposit of 4.5 g/m². After drying, the thermal recording layer was adjusted to a Bekk smoothness of 400-500 sec by calendering. In this way, a thermal recording material was prepared.

EXAMPLE 17

Production of Thermal Recording Material

A thermal recording material was prepared by repeating the procedure of Example 16 except that the α-type crystal modification of 2-m-toluidino-3-methyl-6-di-n-butylaminofluoran used as a color former was replaced by the β-type crystal modification of 2-m-toluidino-3-methyl-6-di-n-butylaminofluoran as produced in Example 3.

COMPARATIVE EXAMPLE 1

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by 2-o-toluidino-3-methyl-6-diethylaminofluoran [compound of formula (2)].

COMPARATIVE EXAMPLE 2

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by 2-m-toluidino-3-methyl-6-diethylaminofluoran [compound of formula (3); m.p. 158°-160° C.].

COMPARATIVE EXAMPLE 3

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by 2-p-toluidino-3-methyl-6-diethylaminofluoran [compound of formula (4)].

COMPARATIVE EXAMPLE 4

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by 2-o-toluidino-3-methyl-6-di-n-butylaminofluoran [compound of formula (5)].

COMPARATIVE EXAMPLE 5

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by 2-p-toluidino-3-methyl-6-di-n-butylaminofluoran [compound of formula (6)].

COMPARATIVE EXAMPLE 6

Production of Pressure-Sensitive Recording Material

An upper leaf was prepared by repeating the procedure of Example 13 except that the α-type crystal modification of 2-m-toluidino-3-methyl-6-di-n-butylaminofluoran used as a color former was replaced by 2-anilino-3-methyl-6-(N-ethyl-N-isobutylamino)fluoran [compound of formula (7) shown below].

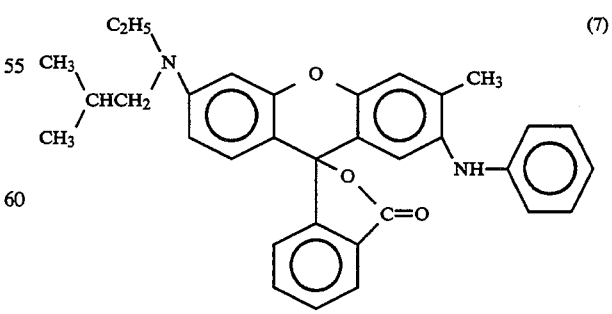

(7)

(Compound of formula (7) is commercially available today as a color former for use with pressure-sensitive recording materials.)

COMPARATIVE EXAMPLE 7

Production of Thermal Recording Material

A thermal recording material was prepared by repeating the procedure of Example 16 except that the α-type crystal modification of 2-m-toluidino-3-methyl-6-di-n-butylaminofluoran used as a color former was replaced by 2-o-toluidino-3-methyl-6-diethylaminofluoran [compound of formula (2)].

COMPARATIVE EXAMPLE 8

Production of Thermal Recording Material

A thermal recording material was prepared by repeating the procedure of Example 16 except that the α-type crystal modification of 2-m-toluidino-3-methyl-6-di-n-butylaminofluoran used as a color former was replaced by 2-m-toluidino-3-methyl-6-diethylaminofluoran [compound of formula (3); m.p. 158°–160° C.].

COMPARATIVE EXAMPLE 9

Production of Thermal Recording Material

A thermal recording material was prepared by repeating the procedure of Example 16 except that the α-type crystal modification of 2-m-toluidino-3-methyl-6-di-n-butylaminofluoran was replaced by 2-p-toluidino-3-methyl-6-diethylaminofluoran [compound of formula (4)].

COMPARATIVE EXAMPLE 10

Production of Thermal Recording Material

A thermal recording material was prepared by repeating the procedure of Example 16 except that the α-type crystal modification of 2-m-toluidino-3-methyl-6-di-n-butylaminofluoran used as a color former was replaced by 2-o-toluidino-3-methyl-6-di-n-butylaminofluoran [compound of formula (5)].

COMPARATIVE EXAMPLE 11

Production of Thermal Recording Material

A thermal recording material was prepared by repeating the procedure of Example 16 except that the α-type crystal modification of 2-m-toluidino-3-methyl-6-di-n-butylaminofluoran used as a color former was replaced by 2-p-toluidino-3-methyl-6-di-n-butylaminofluoran [compound of formula (6)].

COMPARATIVE EXAMPLE 12

Production of Thermal Recording Material

A thermal recording material was prepared by repeating the procedure of Example 16 except that the α-type crystal modification of 2-m-toluidino-3-methyl-6-di-n-butylaminofluoran used as a color former was replaced by 2-anilino-3-methyl-6-(N-ethyl-N-isopentylamino)fluoran [compound of formula (8) shown below].

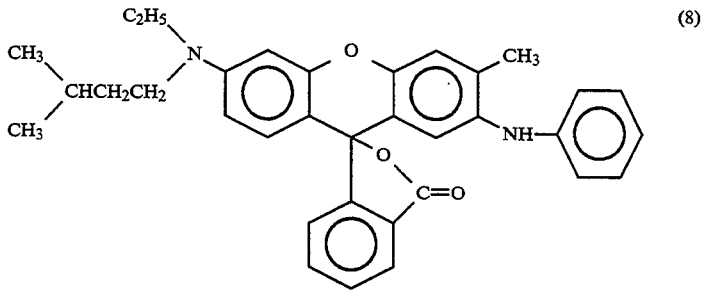

(Compound of formula (8) is commercially available today as a color former for use with thermal recording materials.)

EVALUATION 1

Solubility Test

The α-type crystal modification, β-type crystal modification and toluene adduct of 2-m-toluidino-3-methyl-6-di-n-butylaminofluoran according to the present invention were measured for their solubility in two solvents for pressure-sensitive recording materials, i.e., KMC-113 (dialkylnaphthalene derivatives of Kureha Chemical Industry Co., Ltd.) and SAS-296 (diphenylethane derivatives of Nippon Oil Co., Ltd.) Solubility in those solvents was also measured on the following comparative materials: 2-o-toluidino-3-methyl-6-diethylaminofluoran [compound of formula (2)]; 2-m-toluidino-3-methyl-6-diethylaminofluoran [compound of formula (3); m.p. 158°–160° C.]; 2-p-toluidino-3-methyl-6-diethylaminofluoran [compound of formula (4)]; 2-o-toluidino-3-methyl-6-di-n-butylaminofluoran [compound of formula (5)]; 2-p-toluidino-3-methyl-6-di-n-butylaminofluoran [compound of formula (6)]; and 2-anilino-3-methyl-6-(N-ethyl-N-isobutylamino)fluoran [compound of formula (7)].

Solubility measurements were performed by the following method. A liquid mixture of about 10 w/w % fluoran compound with solvent was heated on a hot plate at 110°±2.5° C. to form a solution. The solution was transferred into a conical flask equipped with a ground stopper and the contents were stirred at 20°±0.1° C. for 48 h. After filtering off the precipitating fluoran compound, about 1 g of the filtrate was weighed accurately and put into a 100-ml measuring flask; thereafter, 95% acetic acid was added to make a total of 100 ml. A 2-ml portion of the resulting solution was put into a 100-ml measuring flask and 95% acetic acid was added to make a total of 100 ml. The absorbance of the colored solution at a wavelength of maximum absorption in the visible range was measured with a spectrophotometer using 95% acetic acid as a control. The amount of the dissolved fluoran compound was determined from a preliminarily constructed calibration curve and the percentage of dissolved amount was calculated. This procedure was repeated for all test samples and the results are shown in Table 1 below.

TABLE 1

| Sample | Dissolved amount (%) | |
| --- | --- | --- |
| | KMC-113 | SAS-296 |
| α-type crystal modification (compound of Example 1) | 9.8 | 9.9 |

TABLE 1-continued

| Sample | Dissolved amount (%) | |
|---|---|---|
| | KMC-113 | SAS-296 |
| β-type crystal modification (compound of Example 2) | 4.7 | 5.1 |
| toluene adduct (compound of Example 6) | ≧10.0 | ≧10.0 |
| compound of formula (2) (comparison) | 0.2 | 0.3 |
| compound of formula (3) (comparison) | 4.2 | 4.0 |
| compound of formula (4) (comparison) | 0.8 | 0.9 |
| compound of formula (5) (comparison) | 2.2 | 4.4 |
| compound of formula (6) (comparison) | 3.3 | 3.5 |
| compound of formula (7) (comparison) | 1.8 | 9.5 |

EVALUATION 2

Testing the Quality and Performance of Pressure-Sensitive Recording Materials

The CB surface of each of the upper leaves prepared in Examples 13, 14 and 15, and Comparative Examples 1–6 was measured for whiteness and tested for lightfastness (the CB surface was the side of the upper leaf onto which the pressure-sensitive coating dispersion was applied). The test and the measurement were conducted by the following methods.

Whiteness

The color density of the CB surface was measured as reflection density (in OD values) with a reflection densitometer RD-914 (Macbeth Instrument Corporation).

Lightfastness

The CB surface was illuminated with a fluorescent lamp ($2 \times 10^4$ lux) for 72 h and the color density of that surface was measured similarly.

Subsequently, another the group of the upper leaves prepared in Examples 13, 14 and 15, and Comparative Examples 1–6 were superposed on lower leaves (having a zinc salt of salicylic acid derivative coated as a color developer) in such a way that the coated surfaces of both leaves would contact each other. Thereafter, the assembly was passed between mini-rollers at a pressure of 100 kgf/cm² to develop a color. The color developed in each sample was checked subjectively. At the same time, the density of each color image (in OD values) was measured with a reflection densitometer RD-914.

In the next place, the lightfastness of the image formed on each sample of the recording materials was tested by the following method.

Lightfastness measurement

Each color image was illuminated with a fluorescent lamp ($2 \times 10^4$ lux) for 72 h and the image density (in OD values) was measured with a reflection densitometer RD-914.

The results of measurements and tests are shown in Table 2.

TABLE 2

| Run No. | Performance of the CB surface | | Image color | Image performance | |
|---|---|---|---|---|---|
| | whiteness (OD) | light-fastness (OD) | | initial color image density (OD) | light-fastness (OD) |
| Example 13 | 0.07 | 0.24 | black | 0.52 | 0.51 |
| Example 14 | 0.07 | 0.23 | black | 0.50 | 0.49 |
| Example 15 | 0.07 | 0.24 | black | 0.51 | 0.50 |
| Comparative Example 1 | 0.11 | 0.29 | purplish black | 0.51 | 0.44 |
| Comparative Example 2 | 0.10 | 0.25 | black | 0.50 | 0.48 |
| Comparative Example 3 | 0.11 | 0.25 | greenish black | 0.47 | 0.43 |
| Comparative Example 4 | 0.11 | 0.26 | reddish black | 0.51 | 0.43 |
| Comparative Example 5 | 0.07 | 0.25 | greenish black | 0.53 | 0.44 |
| Comparative Example 6 | 0.08 | 0.26 | reddish black | 0.43 | 0.39 |

Whiteness of the CB surface

The smaller the value, the higher the whiteness.

Lightfastness of the CB surface

The smaller the value, the higher the lightfastness of the CB surface.

Initial color image density

The greater the value, the higher the initial color density.

Lightfastness of the image

The greater the value, the higher the lightfastness of the image.

EVALUATION 3

Testing the Quality and Performance of Thermal Recording Materials

The whiteness and storage stability of the background of each of the thermal recording materials prepared in Examples 16 and 17, and Comparative Examples 7–12 were tested, and their dynamic sensitivity for color formation was measured by the following methods.

Whiteness of the background

The background color density of each sample was measured as reflection density (in OD values) with a reflection densitometer RD-914 (Macbeth Instrument Corporation)

Heat resistance of the background

Each sample was exposed to 60° C.×20% RH for 72 h and the background color density (in OD values) was measured with a reflection densitometer RD-914.

Lightfastness of the background

Each sample was illuminated with a fluorescent lamp ($2 \times 10^4$ lux) for 72 h and the background color density (in OD values) was measured with a reflection densitometer RD-914.

Dynamic sensitivity for color formation

In recording with a printer TH-PMD (Ohkura Electric Co., Ltd.), the width of pulses that produced an initial color image density of 1.0 in terms of OD values was measured and the value of applied energy was calculated by the following equation.

Conditions of measurement

Applied voltage: 24 V

Resistance at head: 1640 Ω

Applied pulse width: 0.15–1.95 ms

Applied energy (mJ/dot)=Power (W/dot)×applied pulse width

The results of all tests and measurements are shown in Table 3 below.

TABLE 3

| Run No. | Background whiteness (OD) | Background storage stability heat resistance (OD) | Background storage stability light-fastness (OD) | Dynamic sensitivity to color formation (mJ/dot) |
| --- | --- | --- | --- | --- |
| Example 18 | 0.10 | 0.20 | 0.22 | 0.245 |
| Example 17 | 0.10 | 0.19 | 0.21 | 0.256 |
| Comparative Example 7 | 0.11 | 0.12 | 0.4S | 0.279 |
| Comparative Example 8 | 0.13 | 0.15 | 0.29 | 0.254 |
| Comparative Example 9 | 0.14 | 0.17 | 0.82 | 0.272 |
| Comparative Example 10 | 0.20 | 0.24 | 0.22 | 0.265 |
| Comparative Example 11 | 0.19 | 0.33 | 0.30 | 0.265 |
| Comparative Example 12 | 0.14 | 0.21 | 0.24 | 0.252 |

Background whiteness

The smaller the value, the higher the whiteness of the background.

Background storage stability

The smaller the value after each test, the higher the storage stability of the background.

Dynamic sensitivity for color formation

The smaller the value, the higher the sensitivity for color formation.

Subsequently, another group of the thermal recording materials prepared in Examples 16 and 17, and Comparative Examples 7-12 were permitted to develop color on black test charts in a copy mode using a Toshiba FAX model TF-370 and the image density (in OD values) on each sample was measured with the Macbeth RD-914.

In the next place, the image obtained were tested for their storage stability in accordance with the following methods:

Image resistance to hot humidity

Each color image was exposed to 50° C.×90% RH for 72 h and, thereafter, the image density (in OD values) was measured with a reflection densitometer RD-914.

Image resistance to heat

Each color image was exposed to 60° C.×20% RH for 72 h and thereafter, the image density (in OD values) was measured with a reflection densitometer RD-914.

Image lightfastness

Each color image was illuminated with a fluorescent lamp (2×10⁴ lux) for 72 h and, thereafter, the image density (in OD values) was measured with a reflection densitometer RD-914.

The storage stability of each image was expressed by the following formula:

$$\text{Image storage stability} = \frac{\text{Image density after test}}{\text{Initial color image density}}$$

The results of all measurements and tests are shown in Table 4 below.

TABLE 4

| Run No. | Image color | Initial color image density (OD value) | Image storage stability hot humidity resistance | Image storage stability Heat resistance | Image storage stability Light-fastness |
| --- | --- | --- | --- | --- | --- |
| Example 16 | black | 1.38 | 0.96 | 0.95 | 0.97 |
| Example 17 | black | 1.37 | 0.97 | 0.95 | 0.97 |
| Comparative Example 7 | purplish black | 1.34 | 0.87 | 0.92 | 0.91 |
| Comparative Example 8 | black | 1.33 | 0.91 | 0.90 | 0.92 |
| Comparative Example 9 | greenish black | 1.38 | 0.96 | 0.94 | 0.93 |
| Comparative Example 10 | reddish black | 1.33 | 0.87 | 0.85 | 0.92 |
| Comparative Example 11 | greenish black | 1.37 | 0.92 | 0.93 | 0.92 |
| Comparative Example 12 | reddish black | 1.36 | 0.96 | 0.95 | 0.96 |

Initial color image density

The higher the value (in OD values), the higher the initial color density.

Image storage stability

The higher the value, the higher the storage stability of each image.

As one can see from Table 1, the α-type crystal modification, the β-type crystal modification and toluene adduct of the fluoran compound according to the present invention have an outstandingly high solubility in inner-phase solvent(s) compared to compounds having similar structures. As is also clear from Tables 2–4, pressure-sensitive and thermal recording materials that use as color formers the α-type crystal modification, β-type crystal modification and toluene adduct of the fluoran compound according to the present invention have the advantage that the CB surface and the background have a higher degree of whiteness as accompanied by better color rendition than recording materials that use color formers having similar structures. In addition, the recording materials using the color formers of the present invention have higher sensitivity for color formation, better stability of the CB surface and background, and higher storage stability of image. Even when compared with compounds that are commercially available today as color formers, the α-type crystal modification, β-type crystal modification and toluene adduct of the fluoran compound according to the present invention provide good color rendering, as well as high levels of whiteness in the CB surface and the background. In addition, they ensure at least comparable levels of stability not only for the CB surface and the background but also in the storage of image.

Thus, the compounds under consideration are very useful as color formers for pressure-sensitive materials and thermal recording materials.

What is claimed is:

1. An α-type crystal modification of 2-m-toluidino-3-methyl-6-di-n-butylaminofluoran that is characterized by characteristic peaks at diffraction angles at $2\theta \pm 0.2°$ of 8.4°, 9.8°, 17.7°, 21.0° and 22.8° on X-ray diffractiometry using Cu-Kα rays.

2. A α-type crystal modification of 2-m-toluidino-3-methyl-6-di-n-butylaminofluoran that is characterized by characteristic peaks at diffraction angles at $2\theta \pm 0.2°$ of 11.7°, 14.4°, 16.4°, 19.2° and 21.3° on X-ray diffractiometry using Cu-Kα rays.

3. A crystalline toluene adduct of 2-m-toluidino-3-methyl-6-di-n-butylaminofluoran that is characterized by characteristic peaks at diffraction angles at $2\theta \pm 0.2°$ of 5.6°, 9.2°, 11.0°, 16.2°, 18.0° and 23.1° on X-ray diffractiometry using Cu-Kα rays.

4. A process for producing the α-type crystal modification of 2-m-toluidino-3-methyl-6-di-n-butylaminofluoran of claim 1 by treating the crystalline toluene adduct of 2-m-toluidino-3-methyl-6-di-n-butylaminofluoran having characteristic peaks at diffraction angles at 2θ±0.2° of 5.6°, 9.2°, 11.0°, 16.2°, 18.0° and 23.1° on X-ray diffractiometry using Cu-Kα rays in methanol at 0°-60° C.

5. A process for producing the β-type crystal modification of 2-m-toluidino-3-methyl-6-di-n-butylaminofluoran of claim 2 by recrystallizing the α-type crystal modification of 2-m-toluidino-3-methyl-6-di-n-butylaminofluoran having characteristic peaks at diffraction angles at 2θ±0.2° of 8.4°, 9.8°, 17.7°, 21.0° and 22.8° on X-ray diffractiometry using Cu-Kα rays, and/or the crystalline toluene adduct of 2-m-toluidino-3-methyl-6-di-n-butylaminofluoran having characteristic peaks of diffraction angles at 2θ±0.2° of 5.6°, 9.2°, 11.0°, 16.2°, 18.0° and 23.1° on X-ray diffractiometry using CU-Kα rays with at least one solvent selected from among ethanol, isopropyl alcohol, n-butanol and acetonitrile.

6. A process for producing the β-type crystal modification of 2-m-toluidino-3-methyl-6-di-n-butylaminofluoran of claim 2 by dispersing the α-type crystal modification of 2-m-toluidino-3-methyl-6-di-n-butylaminofluoran having characteristic peaks at diffraction angles at 2θ±0.2° of 8.4°, 9.8°, 17.7°, 21.0° and 22.8° on X-ray diffractiometry using Cu-Kα rays, and/or the crystalline toluene adduct of 2-m-toluidino-3-methyl-6-di-n-butylaminofluoran having characteristic peaks at diffraction angles at 2θ±0.2° of 5.6°, 9.2°, 11.0°, 16.2°, 18.0° and 23.1° on X-ray diffractiometry using Cu-Kα rays, in at least one solvent selected from among ethanol, isopropyl alcohol, and n-butanol and treating the dispersion at a temperature ranging from room temperature to the reflux temperature.

7. A process for producing the β-type crystal modification of 2-m-toluidino-3-methyl-6-di-n-butylaminofluoran of claim 2 by treating the crystalline toluene adduct of 2-m-toluidino-3-methyl-6-di-n-butylaminofluoran having characteristic peaks at diffraction angles at 2θ±0.2° of 5.6°, 9.2°, 11.0°, 16.2°, 18.0° and 23.1° on X-ray diffractiometry using Cu-Kα rays, at a temperature of 30°-110° C. under vacuum.

8. A process for producing the crystalline toluene adduct of 2-m-toluidino-3-methyl-6-di-n-butylaminofluoran of claim 3 by precipitating a crystal from a toluene solution of 2-m-toluidino-3-methyl-6-di-n-butylaminofluoran.

9. A process according to claim 8 which comprises reacting a benzophenone compound of formula (I):

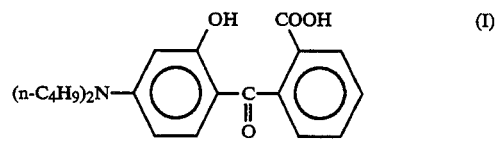

with a diphenylamine compound of formula (II):

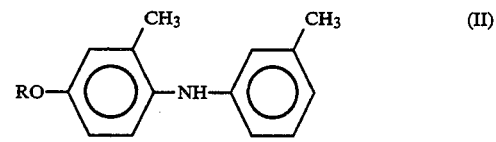

where R is a lower alkyl group in the presence of a dehydrating/condensing agent, treating the reaction product with an alkali, and precipitating a crystal from a toluene extract of the treated product.

10. A process according to claim 8 which comprises dissolving the α-type crystal modification of 2-m-toluidino-3-methyl-6-di-n-butylaminofluoran having characteristic peaks at diffraction angles at 2θ±0.2° of 8.4°, 9.8°, 17.7°, 21.0° and 22.8° on X-ray diffractiometry using Cu-Kα rays, and/or the β-type crystal modification of 2-m-toluidino-3-methyl-6-di-n-butylaminofluoran having characteristic peaks at diffraction angles at 2θ±0.2° of 11.7°, 14.4°, 16.4°, 19.2° and 21.3° on X-ray diffractiometry using CU-Kα rays, in toluene and then precipitating a crystal.

* * * * *

UNITED STATES PATENT AND TRADEMARK OFFICE
CERTIFICATE OF CORRECTION

PATENT NO. : 5,342,967
DATED : August 30, 1994
INVENTOR(S) : Fujita et al

It is certified that error appears in the above-indentified patent and that said Letters Patent is hereby corrected as shown below:

On the Title Page:
In the Abstract, line 2, change "2-n-toluidino-" to --2-m-toluidino--.
Column 1, line 27, change "Inorganic" to --inorganic--.
Column 1, line 34, change "In" to --in--.
Column 11, line 33, change "4.8 g" to --44.8 g--.
Column 21, Table 3, column 1, line 1 after the heading, change "Example 18" to --Example 16--.
Column 21, Table 3, column 4, line 3 after the heading, change "0.4S" to --0.45--.
Column 21, Table 3, column 4, line 5 after the heading, change "0.82" to --0.32--.
Column 22, line 61, change "α-type" to --β-type--.
Column 23, line 22 and Column 24, line 41, change "CU-Kα" to --Cu-Kα-- at both occurrences.

Signed and Sealed this

Thirteenth Day of June, 1995

Attest:

BRUCE LEHMAN

Attesting Officer

Commissioner of Patents and Trademarks